(12) United States Patent
Yokoi et al.

(10) Patent No.: US 8,765,064 B2
(45) Date of Patent: Jul. 1, 2014

(54) STERILE SUBSTANCE SUPPLYING APPARATUS

(75) Inventors: Yasuhiko Yokoi, Ota (JP); Jiro Ohnishi, Ota (JP); Shinji Fukui, Oizumi-machi (JP); Akifumi Iwama, Tsukuba (JP); Hiroshi Yamamoto, Neyagawa (JP); Masaki Harada, Yawata (JP); Tatsuya Hirose, Osaka (JP)

(73) Assignee: Panasonic Healthcare Co., Ltd., Toon-shi (JP)

( * ) Notice: Subject to any disclaimer, the term of this patent is extended or adjusted under 35 U.S.C. 154(b) by 228 days.

(21) Appl. No.: 12/731,708

(22) Filed: Mar. 25, 2010

(65) Prior Publication Data

US 2011/0027131 A1  Feb. 3, 2011

(30) Foreign Application Priority Data

Jul. 30, 2009 (JP) .................................. 2009-178085

(51) Int. Cl.
| | | |
|---|---|---|
| B06B 1/00 | (2006.01) | |
| A61L 2/00 | (2006.01) | |
| A61L 9/00 | (2006.01) | |
| B01J 7/00 | (2006.01) | |

(52) U.S. Cl.
USPC ........... 422/128; 422/127; 422/292; 422/305; 422/306

(58) Field of Classification Search
CPC ................ B06B 1/00; A61L 2/00; A61L 9/00
USPC .......... 422/292, 295, 298, 127, 128, 305, 306
See application file for complete search history.

(56) References Cited

U.S. PATENT DOCUMENTS

| | | | | |
|---|---|---|---|---|
| 4,797,255 A | * | 1/1989 | Hatanaka et al. | ............... 422/28 |
| 5,305,737 A | * | 4/1994 | Vago | ................... 601/4 |
| 6,379,616 B1 | * | 4/2002 | Sheiman | ......................... 422/31 |
| 7,336,019 B1 | * | 2/2008 | Puskas | .......................... 310/317 |

FOREIGN PATENT DOCUMENTS

| | | |
|---|---|---|
| GB | 2395904 A | 6/2004 |
| JP | 56-24977 A | 3/1981 |
| JP | 2005-160903 A | 6/2005 |

(Continued)

OTHER PUBLICATIONS

European Search Report dated Jun. 25, 2010, issued in corresponding European Patent Application No. 10003206.9.

*Primary Examiner* — Regina M Yoo
(74) *Attorney, Agent, or Firm* — Westerman, Hattori, Daniels & Adrian, LLP

(57) ABSTRACT

A sterile-substance-supplying apparatus comprising: an atomization unit including a reservoir unit to reserve hydrogen peroxide, and an ultrasound vibrator to impart ultrasound vibration to the reserved hydrogen peroxide to be atomized; an evaporation unit, provided above the reservoir unit, that heats the atomized hydrogen peroxide to be evaporated; a connecting member connecting the evaporation unit and the atomization unit to each other; a hydrogen-peroxide-supply port to allow the hydrogen peroxide to be supplied to the reservoir unit; a carrier-gas-supply port, provided at the connecting member, that allows carrier gas for allowing the atomized hydrogen peroxide to flow to the evaporation unit to be supplied; and a container portion to reserve a substance for transmitting the ultrasound vibration generated by the ultrasound vibrator, and a metal vibrating plate, provided at a bottom portion of the reservoir unit, that transmits to the hydrogen peroxide the ultrasound vibration transmitted through the substance.

5 Claims, 15 Drawing Sheets

(56) References Cited

FOREIGN PATENT DOCUMENTS

| | | |
|---|---|---|
| JP | 2005-312799 A | 11/2005 |
| JP | 2006-320392 A | 11/2006 |
| JP | 2007-534132 A | 11/2007 |
| JP | 2010-46226 A | 4/2010 |
| JP | 2010-69255 A | 4/2010 |
| WO | 99/42145 A1 | 8/1999 |
| WO | 2007/014435 A1 | 2/2007 |
| WO | 2010/021139 A1 | 2/2010 |

* cited by examiner

STERILE SUBSTANCE SUPPLYING APPARATUS

CROSS-REFERENCE TO RELATED APPLICATION

This application claims the benefit of priority to Japanese Patent Application No. 2009-178085, filed Jul. 30, 2009, of which full contents are incorporated herein by reference.

BACKGROUND OF THE INVENTION

1. Field of the Invention

The present invention relates to a sterile substance supplying apparatus for an isolator.

2. Description of the Related Art

An isolator has therein a working chamber maintained in an aseptic environment and used for work requiring the working chamber to be kept in an aseptic environment such as for work on material originating from a living body such as a cell culture, for example. Here, an aseptic environment refers to an environment that is almost completely dust-free and germ-free in order to avoid mixing of substances other than those required for the work performed in the working chamber. Also, sterilization treatment refers to treatment for realizing an aseptic environment, and substances used for sterilization treatment is referred to as sterile substances.

The working chamber is provided with a gas supply port and a gas discharge port, and air is supplied through the gas supply port into the working chamber, and discharged through the gas discharge port. In general, an isolator has a particulate collecting filter such as an HEPA filter disposed at the gas supply port in order to ensure an aseptic environment in the working chamber, and air is supplied into the working chamber through this particulate collecting filter. The particulate collecting filter is also disposed at the gas discharge port, and air in the working chamber is discharged from the working chamber through the particulate collecting filter.

Also, in the isolator, a sterile substance such as hydrogen peroxide is sprayed into the working chamber to perform sterilization treatment for sterilizing the interior of the working chamber (See Japanese Patent Laid-Open No. 2006-320392 and Japanese Patent Laid-Open No. 2005-312799).

During sterilization treatment, gaseous sterilized substance is supplied into the working chamber. When sterilization treatment is performed in the above isolator, a long preparation time is required for turning the sterile substance into a gaseous state, which lengthens the entire time required for sterilization treatment leading to a problem of reducing the work efficiency of the isolator.

SUMMARY OF THE INVENTION

A sterile substance supplying apparatus according to an aspect of the present invention, comprises: an atomization unit including a reservoir unit configured to reserve hydrogen peroxide, and an ultrasound vibrator configured to impart ultrasound vibration to the hydrogen peroxide reserved in the reserved portion to be atomized; an evaporation unit provided above the reservoir unit, the evaporation unit configured to heat the hydrogen peroxide atomized by the atomization unit to be evaporated; a connecting member connecting the evaporation unit and the atomization unit to each other; a hydrogen peroxide supply port configured to allow the hydrogen peroxide to be supplied to the reservoir unit; a carrier gas supply port provided at the connecting member, the carrier gas supply port configured to allow carrier gas to be supplied, the carrier gas allowing the atomized hydrogen peroxide to flow to the evaporation unit; and a container portion configured to reserve a substance for transmitting the ultrasound vibration generated by the ultrasound vibrator, and a metal vibrating plate provided at a bottom portion of the reservoir unit, the metal vibrating plate configured to transmit to the hydrogen peroxide the ultrasound vibration transmitted through the substance.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which.

DETAILED DESCRIPTION OF THE INVENTION

At least the following details will become apparent from descriptions of this specification and of the accompanying drawings A sterile substance supplying apparatus according to the present embodiment is provided with: an atomization unit including a reservoir unit reserving hydrogen peroxide and an ultrasound vibrator for atomizing the hydrogen peroxide by imparting ultrasound vibration to the hydrogen peroxide reserved in the reserved portion; an evaporation unit heating and evaporating the hydrogen peroxide atomized by the atomization unit; a connecting member connecting the evaporation unit and the atomization unit to each other; a sterile substance supply port for supplying the hydrogen peroxide to the reservoir unit; a carrier gas supply port disposed at the connecting member to supply carrier gas to allow the atomized hydrogen peroxide to flow to the evaporation unit; and a container portion in which a substance for transmitting the ultrasound vibration generated by the ultrasound vibrator is reserved, in which the evaporation unit is disposed above the reservoir unit, and a stainless steel vibrating plate, transmitting to the hydrogen peroxide the ultrasound vibration transmitted through the substance is detachably provided to a bottom portion of the reservoir unit.

According to the sterile substance supplying apparatus of the present embodiment, employment of a two-stage method in which hydrogen peroxide is first atomized by the atomization unit having an ultrasound transducer and then evaporated by the evaporation unit, allows quick gasification of hydrogen peroxide. Therefore, less heat quantity is input to the evaporation unit than before. As a result, the time required for gasifying hydrogen peroxide can be reduced which in turn reduces the time required for the entire sterilization treatment. As a result, work efficiency of the isolator can be improved.

The isolator according to the present embodiment, which will be described below, has a working chamber where work on material originating from a living body is performed, a gas supply unit for supplying a gas into the working chamber, a gas discharge portion for discharging gas in the working chamber, and a particulate collecting filter and is further provided with a flow path for flowing the gas supply unit with the working chamber, and a sterile substance supplying apparatus for supplying sterile substances into the working chamber.

According to the present embodiment, the time required for sterilization treatment can be reduced, and the work efficiency of the isolator improved.

First Embodiment

Figure 1:
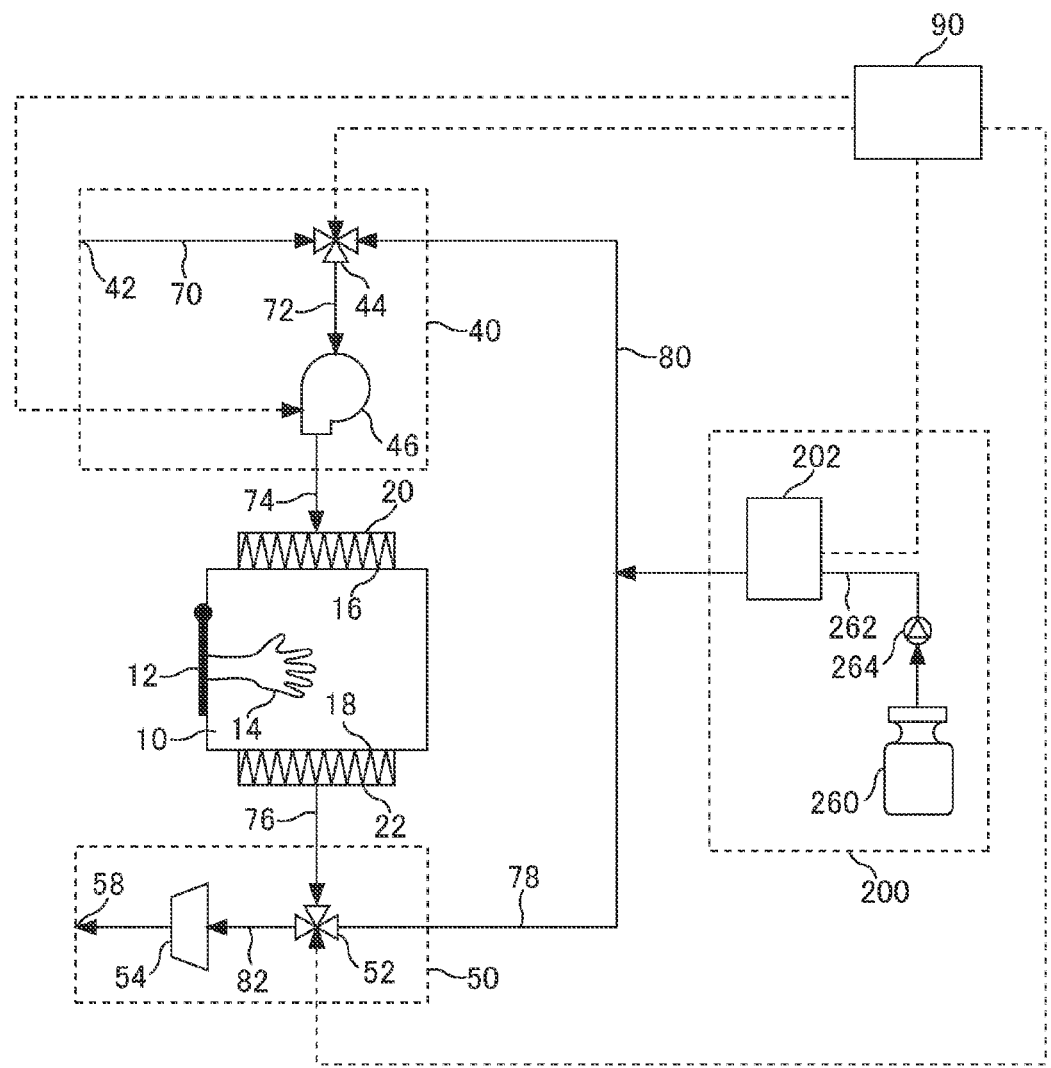
FIG. 1 is a diagram illustrating a configuration of an isolator.

A general configuration of an isolator 100 shown as the first embodiment is illustrated in FIG. 1. As shown in FIG. 1, the isolator 100 is provided with a working chamber 10 where work such as cell extraction and cell culture using a material deriving from a living substance is performed, a gas supply unit 40 for supplying gas into the working chamber 10, a gas discharge portion 50 for discharging gas in the working chamber 10, a sterile substance supplying apparatus 200 for supplying sterile substances into the working chamber 10, and a control unit 90 for controlling each of these components. Note that material originating from a living body refers to material including a living organism itself including cells, a substance constituting a living organism, a substance produced by a living organism or the like.

The gas supply unit 40 is provided with an air inlet 42, a three-way valve 44, and a fan 46. Air is taken in from the outside through the air inlet 42. The three-way valve 44 is connected on the downstream side of the gas-flow flowing from the air inlet 42 and through path 70 and on the downstream side of the gas-flow flowing from the sterile gas generator 202 and through path 80. Also, the three-way valve 44 is connected to the upstream side of the gas-flow flowing toward the fan 46 through path 72. The three-way valve 44 is capable of exclusive switching between a gas flow flowing from path 70 toward path 72 and that from path 80 toward path 72. The air taken in through the air inlet 42 and gas containing sterile substances fed through path 80 are taken into the fan 46 through the three-way valve 44.

Gas taken in from the three-way valve 44 through path 72 is fed by the fan 46 to flow through path 74 toward the working chamber 10. The fan 46 is capable of on/off switching control by the control unit 90. The fan 46 is capable of adjusting the amount of discharge continuously.

A front door 12 capable of being opened/closed is disposed to the working chamber 10. Work gloves 14 are provided at a predetermined position on the front door 12 for a worker to perform work in the working chamber 10. A worker by inserting his/her hands into the work gloves 14 through an opening, not shown, provided at the front door 12 is enabled to perform work in the working chamber 10. Gas fed out from the fan 46 is taken into the working chamber 10 through the gas supply port 16 and discharged through the gas discharge port 18.

An HEPA filter 20 is disposed to the gas supply port 16 and an HEPA filter 22 is disposed to the gas discharge port 18. The aseptic state of the working chamber 10 is ensured by the filters. The gas in the working chamber 10 is discharged through the gas discharge port 18, the HEPA filter 22, and path 76 to the discharge portion 50.

The gas discharge portion 50 has provided thereto a three-way valve 52, a sterile substance reduction treatment unit 54, and a discharge port 58 in this order along the gas flow.

The three-way valve 52 is connected on the downstream side of the gas-flow flowing from the working chamber 10 and through path 76 and on the upstream side of the gas-flow flowing through path 82 toward the sterile substance reduction treatment unit 54. The three-way valve 52 is connected on the upstream side of the gas-flow flowing through path 78 toward the sterile substance supplying apparatus 200, which will be described later. The three-way valve 52 is capable of exclusive switching between a gas flow flowing from path 76 to path 82 and that from path 76 to path 78, and gas taken in from path 76 is sent toward path 82 or path 78.

The sterile substance reduction treatment unit 54 performs treatment for reducing the concentration of sterile substances contained in the gas sent out through the three-way valve 52. The sterile substance reduction treatment unit 54 may include a metal catalyst such as platinum, activated coal or the like, for example.

A sterile substance supplying apparatus 200 for supplying a sterile substance to the working chamber 10 is provided outside the working chamber 10. The sterile substance supplying apparatus 200 keeps the working chamber 10 and the path in an aseptic environment by supplying sterile substances (hydrogen peroxide ($H_2O_2$) in the present embodiment) to the working chamber 10 and circulating them in the isolator 100. Note that, an aseptic environment refers to an environment that is almost completely dust-free and germ-free where mixing of substances other than those required for the work to be performed in the working chamber is prevented.

The sterile substance supplying apparatus 200 is connected on the downstream side of the gas-flow flowing from the three-way valve 52 and through path 78, and on the upstream side of the gas-flow flowing through path 80 toward the three-way valve 44. The sterile substance supplying apparatus 200 has a sterile substance cartridge 260, a pump 264 (peristaltic pump, for example), and a sterile gas generator 202. The sterile substance cartridge 260 stores therein hydrogen peroxide solution as a sterile substance. The pump 264 pumps up the hydrogen peroxide solution stored in the sterile substance cartridge 260 and feeds it out to the sterile gas generator 202. The sterile gas generator 202 evaporates (vaporizes) the hydrogen peroxide solution supplied and generates hydrogen peroxide gas. The generated hydrogen peroxide gas is fed out to path 80.

Figure 2A:
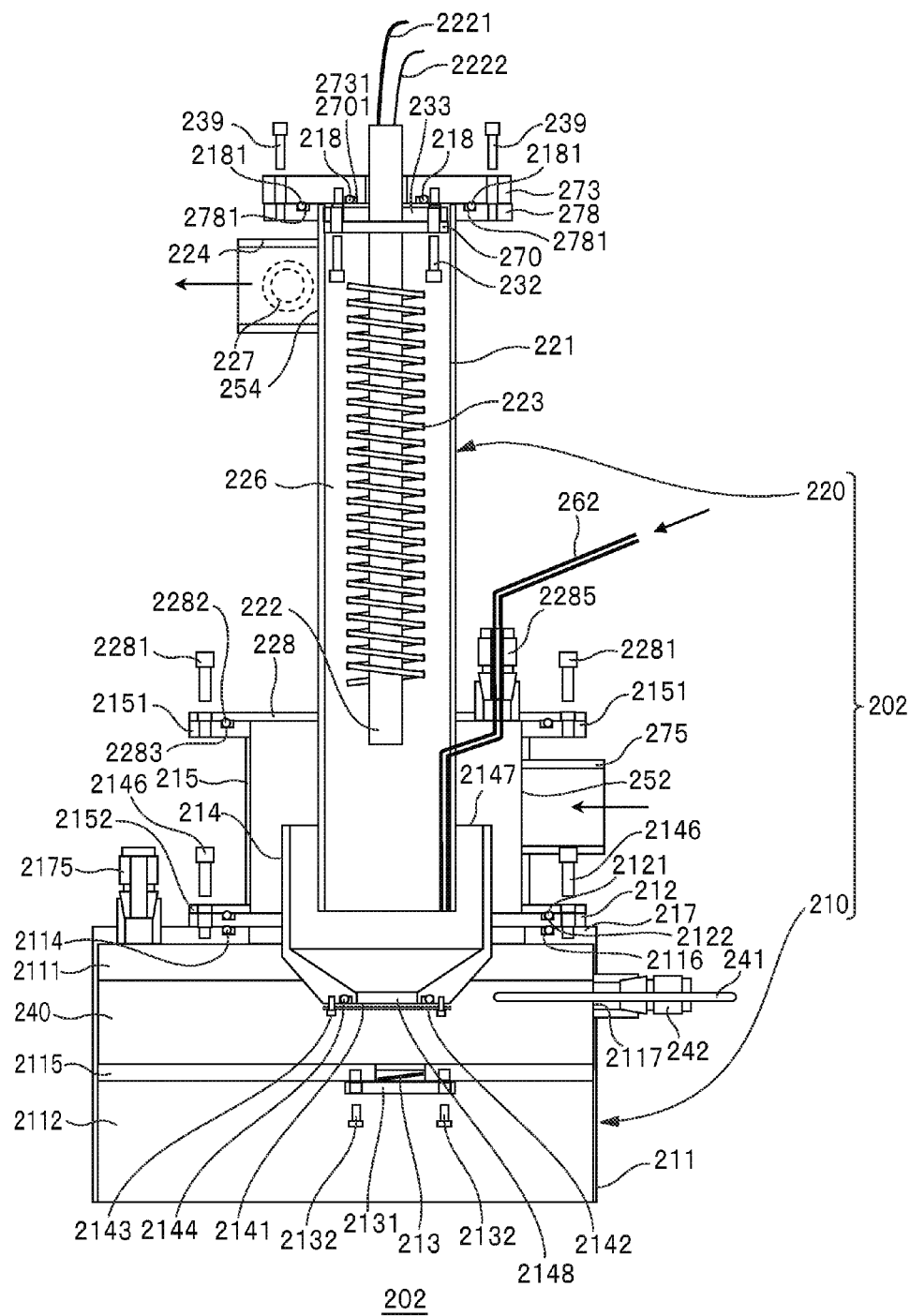
FIG. 2A is a diagram illustrating a configuration of a sterile gas generator of the first embodiment.
Figure 2B:
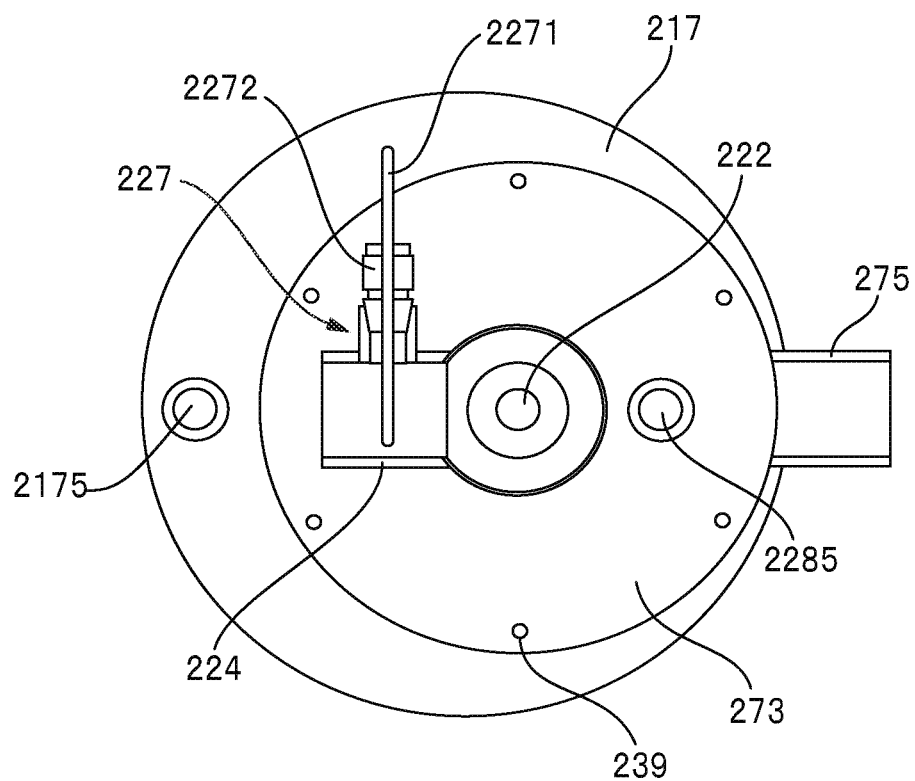
FIG. 2B is a diagram (partially cut away) of the sterile gas generator of the first embodiment seen from above.

FIGS. 2A and 2B show a configuration of the sterile gas generator 202. FIG. 2A is a sectional view of the sterile gas generator 202 seen from the side, while FIG. 2B is a diagram of the sterile gas generator 202 seen from above (partially cut away).

As shown in FIG. 2A, the sterile gas generator 202 includes an atomization unit 210 and an evaporation unit 220. As shown in FIG. 2A, the atomization unit 210 is configured to include a container unit 211, an ultrasound vibrator 213, a cup 214 (reservoir unit), a vibrating plate 2141, a cylindrical member 215 (connecting member) and the like.

The container unit 211 is a hollow cylindrical container with an opening on top and made of metal such as stainless steel or resin. A circular partition plate 2115 for dividing the interior of the container unit 211 is provided inside the container unit 211, and two spaces are formed inside the container unit 211 by this partition plate 2115. Hereinafter the space formed on the upper side of the partition plate 2115 is referred to as a first space 2111, while the space formed on the lower side is referred to as a second space 2112.

In the first space 2111 of the two spaces, there is stored a substance for transmitting an ultrasound wave emitted from the ultrasound vibrator 213 to the vibrating plate 2141 (hereinafter referred to as an ultrasound propagation substance 240). Note that, liquid with small viscosity such as water is suitable as the ultrasound propagation substance 240.

An opening 2117 is disposed on the side face of the first space 2111 of the container unit 211, and a thermometer 241 for measuring the temperature of the ultrasound propagation substance 240 and a fitting 242 for holding the same are provided at the opening 2117. The temperature measured by the thermometer 241 is transferred to the control unit 90. If the temperature of the ultrasound propagation substance 240 exceeds a predetermined temperature, the control unit 90 stops supplying power to the ultrasound vibrator 213. There is disposed at a predetermined position of the top plate 217 of the container unit 211, a plug 2175 for supplying the ultrasound propagation substance 240 to the first space 2111, and adjusting the internal pressure in first space 2111 and the like.

The ultrasound vibrator 213 is disposed at a predetermined position on the partition plate 2115 of the container unit 211.

The ultrasound vibrator 213 is an element for generating ultrasound vibration by drive power such as electricity. As shown in FIG. 2A, the ultrasound vibrator 213 is held inside a container body 2131 with a structure in which two plate-shaped members with different diameters are stacked, and the container body 2131 is fixed to the partition plate 2115 by screws 2132 from the underside.

The cup 214 functions as a reservoir unit for the sterile substance. As shown in FIG. 2A, the cup 214 is a substantially cylindrical container and has openings 2147 and 2148 at the top and bottom. As shown in FIG. 2A, the cup 214 is in a shape of a frustum of a cone (a shape obtained by cutting off a top portion of a cone in a horizontal direction) whose outer diameter decreases toward the bottom.

A thin disc-shaped vibrating plate 2141 is mounted to the lower opening 2148 of the cup 214 to block the opening. The material of the vibrating plate 2141 is metal such as stainless steel (with a thickness of approximately 0.02 mm, for example) or resin (with a thickness of approximately 0.2 mm, for example) or glass, ceramic, carbon graphite and the like. As shown in FIG. 2A, the vibrating plate 2141 is detachably mounted to the cup 214 by assembling an annular flat plate 2142 from below and fixing its peripheral edges to the edge portion of the bottom-face of the cup 214 together with the flat plate 2142 by screws 2143.

Figure 3A:
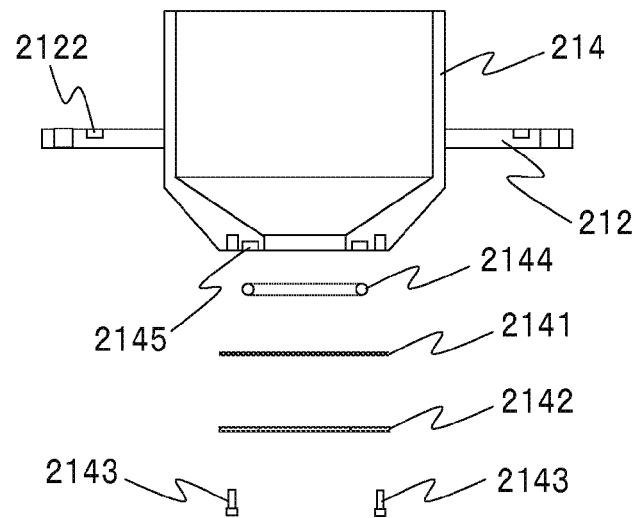
FIG. 3A is an exploded view of the sterile gas generator of the first embodiment including a cup, an O-ring, a vibrating plate, and a flat plate.
Figure 3B:
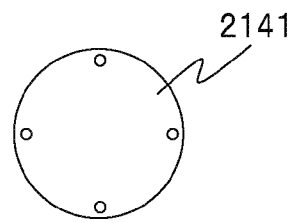
FIG. 3B is a plan view of the vibrating plate of the sterile gas generator of the first embodiment.
Figure 3C:
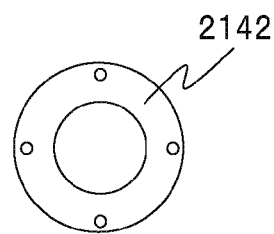
FIG. 3C is a plan view of the flat plate of the sterile gas generator of the first embodiment.

In order to reliably shut the first space 2111 of the container unit 211 from the internal space of the cup 214, an O-ring 2144 is interposed between the mating faces of the vibrating plate 2141 and the cup 214, and an annular groove 2145 for containing the O-ring 2144 is provided to the edge portion at the bottom of the cup 214. FIG. 3A shows a state in which the cup 214, the O-ring 2144, the vibrating plate 2141, and the flat plate 2142 are disassembled. Also, FIG. 3B shows a plan view of the vibrating plate 2141, and FIG. 3C shows a plan view of the flat plate 2142, respectively.

As shown in FIG. 2A, a flange 212 is formed around the side face of the cup 214. The cup 214 is assembled on the container unit 211 by fixing the flange 212 portion to the top plate 217 of the container unit 211 by screws 2146. In order to ensure hermeticity of the first space 2111, an O-ring 2114 is interposed between the upper face of the flange 212 and the container unit 211, and at a portion on the upper face of the container unit 211 to which the flange 212 is brought into contact, an annular groove 2116 is disposed to contain the O-ring 2114.

As shown in FIG. 2A, the cylindrical member 215 is a hollow cylindrical member whose top and bottom faces are open. A flange 2151 is provided around the top face of the cylindrical member 215, while a flange 2152 is provided around the bottom face of the cylindrical member 215, respectively. Flange 228 of a heat pipe 221, which will be described later, is fixed on the top surface of the flange 2151 of the cylindrical member 215, and the opening at the top of the cylindrical member 215 is closed by the flange 228.

The cylindrical member 215 is assembled above the container unit 211 by fixing the flange 2152 at the bottom face to the top plate 217 of the container unit 211 together with the flange 212 of the cup 214 by screws 2146. In order to ensure hermeticity inside the cylindrical member 215, an O-ring 2121 is interposed between the upper face of the flange 212 of the cup 214 and the flange 2152 of the cylindrical member 215. An annular groove 2122 for containing this O-ring 2121 is provided at a portion on the upper face of the flange 212 of the cup 214 to which the flange 2152 of the cylindrical member 215 is brought into contact.

A pipe 275 for allowing carrier gas (air in the present embodiment) fed out from an air supply fan, not shown, to flow into the cylindrical member 215 is connected to the side face of the cylindrical member 215.

In the atomization unit 210 with the above configuration, hydrogen peroxide solution supplied to the cup 214 is atomized by ultrasound vibration input from the ultrasound vibrator 213 through the ultrasound propagation substance 240, and the atomized hydrogen peroxide solution is fed into the evaporation unit 220. Droplets of hydrogen peroxide solution not atomized but adhering to the inner surface of the evaporation unit 220 would drop into the cup 214 by action of gravity and are exposed to ultrasound vibration again to be atomized.

A traveling direction of a wavefront of the ultrasound vibration generated by the ultrasound vibrator 213, that is, the normal at the surface center of the vibrator of the ultrasound vibrator 213 is inclined by a predetermined angle (approximately 7 degrees, for example) with respect to the vertical direction (direction in which gravity acts). In this way, interference between the hydrogen peroxide solution having been atomized first and the later described water column can be prevented, and atomization of hydrogen peroxide solution can be performed in a stable manner.

As shown in FIG. 2A, the evaporation unit 220 is provided above the atomization unit 210. The evaporation unit 220 is configured to include a heat pipe 221, a heater 222, a pipe 224, and a temperature measuring unit 227.

As shown in FIG. 2A, the profile of the heat pipe 221 is in a hollow tubular shape (hollow cylindrical shape in this embodiment). The heat pipe 221 is assembled on the container unit 211 with its axis directed in the vertical direction. The heat pipe 221 is mounted on the cylindrical member 215 by fixing the flange 228 formed around its side face to the flange 2151 of the cylindrical member 215 with screws 2281. In order to ensure hermeticity of the cylindrical member 215, an O-ring 2282 is interposed between the flange 228 of the heat pipe 221 and the upper face of the flange 2151 of the cylindrical member 215. At a portion on the top face of the flange 2151 to which the flange 228 is brought into contact, an annular groove 2283 for containing this O-ring 2282 is provided.

Inside the heat pipe 221, there is formed a flow path 226 through which carrier gas and hydrogen peroxide solution flow from the lower side of the heat pipe 221 toward the upper side thereof. As shown in FIG. 2A, a drain 262 is provided to penetrate through the flange 228 of the heat pipe 221 and the side face of the heat pipe 221. The hydrogen peroxide solution stored in the cup 214 is supplied whenever necessary from the sterile substance cartridge 260 through the drain 262. One end of the drain 262 is located inside the heat pipe 221 at substantially the bottom end thereof. The other end of the drain 262 is connected to the pump 264 shown in FIG. 1. The drain 262 is held by a fitting 2285 provided to the flange 228 of the heat pipe 221. In order to keep the heat pipe 221 hermetic, the peripheral portion of the side face of the heat pipe 221 through which the drain 262 penetrates is sealed with resin material, rubber material or the like.

As shown in FIG. 2A, the bottom end of the heat pipe 221 is located at a position lower than the lowermost end of the opening 252 of the cylindrical member 215 (carrier gas supply port) into which the carrier gas flows. By setting the lower end of the heat pipe 221 at such position, turbulence of the carrier gas can be prevented. Also, the pipe 275 is provided in a positional relationship where the axis of the pipe 275 does not cross the axis of the heater 222 (or the axis of the cylindrical member 215). In this way, the flow of the carrier gas is directed downward in the space between the heat pipe 221 and the cylindrical member 215, and the carrier gas flows around the heat pipe 221 in either a clockwise direction or a counterclockwise direction to generate a swirling upward flow within the heat pipe 221. This upward flow acts to form a stable water column of hydrogen peroxide solution.

The lower end position of the heat pipe 221 is set to a height so that the side face of the heat pipe 221 blocks the hydrogen peroxide solution, vibrated by the ultrasound vibration, from scattering out from the cup 214. More specifically, it is set to a height where a straight line connecting an arbitrary point on the vibration face of the vibrating plate 2141 exposed in the cup 214 and an arbitrary point at the top end of the wall of cup 214 surely crosses the side face of the heat pipe 221. By setting the lower end position of the heat pipe 221 at that height, the water column formed to be directed toward the top opening of the cup 214 is surely blocked by the side face of the heat pipe 221. In this way, the hydrogen peroxide solution is prevented from scattering out from the cup 214 and remains inside the cylindrical member 215, so that hydrogen peroxide solution does not become a target of evaporation to be wasted.

In the sterile gas generator 202 with the above configuration, since the heat pipe 221 is disposed immediately above the cup 214, when the atomized hydrogen peroxide solution bonds again to become droplets inside the heat pipe 221, the droplets drop into the cup 214 by action of gravity and are atomized again to be fed to the heat pipe 221. Thus, the hydrogen peroxide solution can be atomized and evaporated without waste.

Inside the heat pipe 221, there is disposed a heater 222 with a columnar outer diameter extending in the axial direction (vertical direction) of the heat pipe 221. A power supply line 2221 for supplying power to the heater 222 and a temperature measurement wire 2222 used for measuring the temperature of the heater 222 extend out from the upper end of the heater 222. The temperature measurement wire 2222 is connected to the control unit 90.

A plate-shaped helical fin 223 (heat transfer body) made of a material such as stainless steel is disposed to extend continuously in the axial direction (vertical direction) of the heat pipe 221 around the heater 222, to increase the contact area between the hydrogen peroxide solution flowing through the flow path 226 and the heater 222. With such configuration, heat of the heater 222 can be efficiently transferred to the hydrogen peroxide solution enabling quick evaporation of the hydrogen peroxide solution.

A flange 270 is disposed at the upper part of the heater 222. A lid member 273 for closing the top opening of the heat pipe 221 is fixed to this flange 270. An O-ring 218 is interposed between the flange 270 and the lid member 273 to ensure hermeticity of the heat pipe 221. Annular grooves 2701 and 2731 for containing the O-ring 218 are provided at the upper surface of the flange 270 of the heater 222 and the lower surface of the lid member 273.

The central area of the lid member 723 is open through which the upper part of the heater 222 penetrates. The heater 222 is fixed to the lid member 273 by screws 232. In order to prevent heat of the heater 222 from escaping toward the lid member 273, insulation material 233 is interposed between the heater 222 and the lid member 273.

The lid member 273 is mounted by screws 239 on the top side of the flange 278 of the heat pipe 221. An O-ring 2181 is interposed between the flange 278 and the lid member 273 to ensure hermeticity of the heat pipe 221. An annular groove 2781 for containing this O-ring 2381 is provided on the upper surface of the flange 278.

An opening 254 is provided at the upper side face of the heat pipe 221, to which one end of the pipe 224 is connected. A temperature measuring unit 227 for measuring the temperature inside the pipe 224 is provided to the pipe 224. As shown in FIG. 2B, the temperature measuring unit 227 is configured to include a thermometer 2271 and a fitting 2272 for holding the same, and the value measured by the thermometer 2271 is transferred to the control unit 90. The heater 222 is on/off controlled by the control unit 90, and the temperature is controlled so that the temperature read by the temperature measuring unit 227 is approximately 180° C. In the temperature control process, the control unit 90 stops supplying power to the heater 222 when the temperature of the heater 222 exceeds a predetermined temperature (700° C., for example).

<Description of Operation>

Description of operation for generating sterile gas with the sterile gas generator 202 with the above configuration will follow with reference to the timing chart shown in FIG. 4. Generation of sterile gas with the sterile gas generator 202 is controlled by the control unit 90.

First, the switch of the heater 222 is turned on at time t1, and upon start of the operation of the air supply fan, blowing of the carrier gas is started. As a result, heating by the heater 222 is started, with the pump 264 driven to pump up the hydrogen peroxide solution stored in the sterile substance cartridge 260, and feeding hydrogen peroxide solution out toward the cup 214.

Also, when the switch of the heater 222 is turned on, the internal temperature of the pipe 224 starts to rise from normal temperature. When the hydrogen peroxide solution passes through the drain 262 to reach the cup 214 at time t2, the hydrogen peroxide solution starts to collect at the bottom of the cup 214, and the amount of hydrogen peroxide solution in the cup 214 starts to increase.

When the internal temperature of the pipe 224 reaches the evaporation temperature of hydrogen peroxide at time t3, driving of the ultrasound vibrator 213 is started, and the ultrasound vibration is propagated to the cup 214 through the ultrasound propagation liquid 240. As a result, the hydrogen peroxide solution is atomized in the cup 214, and the atomized hydrogen peroxide solution is supplied to the heat pipe 221 by the carrier gas. The atomized hydrogen peroxide solution having been supplied to the heat pipe 221 is heated by the heater 222 and gasified. The gasified hydrogen peroxide gas is supplied to the path 80 through the pipe 224.

Note that, since atomization efficiency varies according to the distance between the surface of the vibrator and the level of liquid to be atomized in the atomizing device using the ultrasound vibrator, it is known that an appropriate distance needs to be maintained. Thus, at time t3 and after, it is preferable that the flow rate of hydrogen peroxide solution fed toward the cup 214 by the pump 264 is adjusted so as to replenish the hydrogen peroxide solution in the cup 214, which is consumed with the progress of atomization and evaporation. As a result at time t3 and after, the hydrogen peroxide solution in the cup 214 can be efficiently atomized. The total amount of hydrogen peroxide solution to be fed out toward the cup 214 is determined in advance, and the driving of the pump 264 is stopped after a predetermined time has elapsed according to the capacity of the pump 264.

When the driving of the pump 264 stops at time t3 or later, replenishment of the hydrogen peroxide solution to the cup 214 is stops at time t4. The amount of the hydrogen peroxide solution in the cup 214 gradually decreases at time t4 and after, and the amount of hydrogen peroxide solution remaining in the cup 214 reaches zero at time t5.

Since the amount of atomized hydrogen peroxide solution to be fed from the atomization unit 210 to the evaporation unit 220 gradually decreases at time t5 or after, the heat lost by evaporation of the hydrogen peroxide solution in the heat pipe 221 gradually decreases. As a result, the internal temperature in the pipe 224 is further raised from the evaporation temperature of the hydrogen peroxide solution. In other words, an increase in the internal temperature in the pipe 224 is a phenomenon indicating that the amount of the hydrogen peroxide solution remaining in the cup 214 has reached nil, and by detecting this phenomenon, the amount of hydrogen peroxide solution remaining in the cup 214 can be estimated whether it is nil or not. When the internal temperature of the pipe 224 measured by the thermometer 225 reaches a predetermined determination temperature at time t6, the driving of the ultrasound vibrator 213 is stopped, and the switch of the heater 222 is turned off to stop heating by the heater 222.

Note that the predetermined temperature is the internal temperature in the pipe 224 when gasification of hydrogen peroxide solution in the heat pipe 221 is completed and only the carrier gas starts to move in the heat pipe 221. That is, the fact that the internal temperature of the pipe 224 reaches the predetermined determination temperature means that the amount of hydrogen peroxide solution remaining in the cup 214 reaches nil and hydrogen peroxide solution to be gasified does not exist in the sterile gas generator 202.

At time t6 and after, the internal temperature of the pipe 224 continues to rise and the gradually decreases to return to the normal temperature at time t7.

Note that, the period from time t1 to time t3 is the preparation time required for generating sterile gas. Atomization of the hydrogen peroxide solution in the atomization unit 210 is performed during time t3 and time t4. The path including the working chamber 10 is exposed to sterile gas (the pretreatment process and the sterilization process to be described later) during time t1 and time t7. Sterile gas is discharged from the path including the working chamber 10 (the substitution process to be described later) at time t7 and after.

Returning to FIG. 1, description on the control unit 90 will be given.

The control unit 90 controls the delivery of sterile gas by the sterile gas generator 202 as mentioned above. Also, the control unit 90 switches gas paths by controlling the opening/closing of the three-way valves 44 and 52.

Specifically, the control unit 90 controls exclusive switching between gas flows flowing from path 70 toward path 72 and that from path 80 toward path 72 by controlling the opening/closing of the three-way valve 44. Also, the control unit 90 controls exclusive switching between gas flows flowing from path 76 toward path 82 and that from path 76 toward path 78 by controlling opening/closing of the three-way valve 52.

<Switching of Gas Flow>

The gas flow path in the isolator 100 is switched between the following two options by controlling opening/closing of the three-way valves 44 and 52 by the control unit 90. That is, in a case the hydrogen peroxide gas is circulated in the isolator 100, the three-way valve 44 is open for the flow to flow only from path 80 toward path 72 and closed between from path 70 to path 72. And the three-way valve 52 is open for the flow to flow only from path 76 toward the path 78 and closed between from path 76 and path 82.

The other is, in a case substitution of air in the working chamber is performed, the three-way valve 44 is open for the flow to flow only from path 70 toward path 72 and closed between path 80 and path 72. And the three-way valve 52 is open for the flow to flow only from path 76 toward path 82 and closed between path 76 and path 78. In this way, a path is formed where air flows from the air inlet 42 through path 70, the three-way valve 44, path 72, the fan 46, path 74, the HEPA filter 20, and the gas supply port 16 to enter the working chamber 10 and further flows through the gas discharge port 18, the HEPA filter 22, path 76, the three-way valve 52, path 82, and the sterile substance reduction processing unit 54 to be discharged from the discharge port 58.

<Sterilization Treatment>

In the isolator 100, after one work is completed in the working chamber 10, sterilization treatment in the working chamber 10 and the flow paths used for the previous work is performed before starting the subsequent work. Sterilization treatment includes a pretreatment process, an exposure process, and a substitution process.

Figure 4:
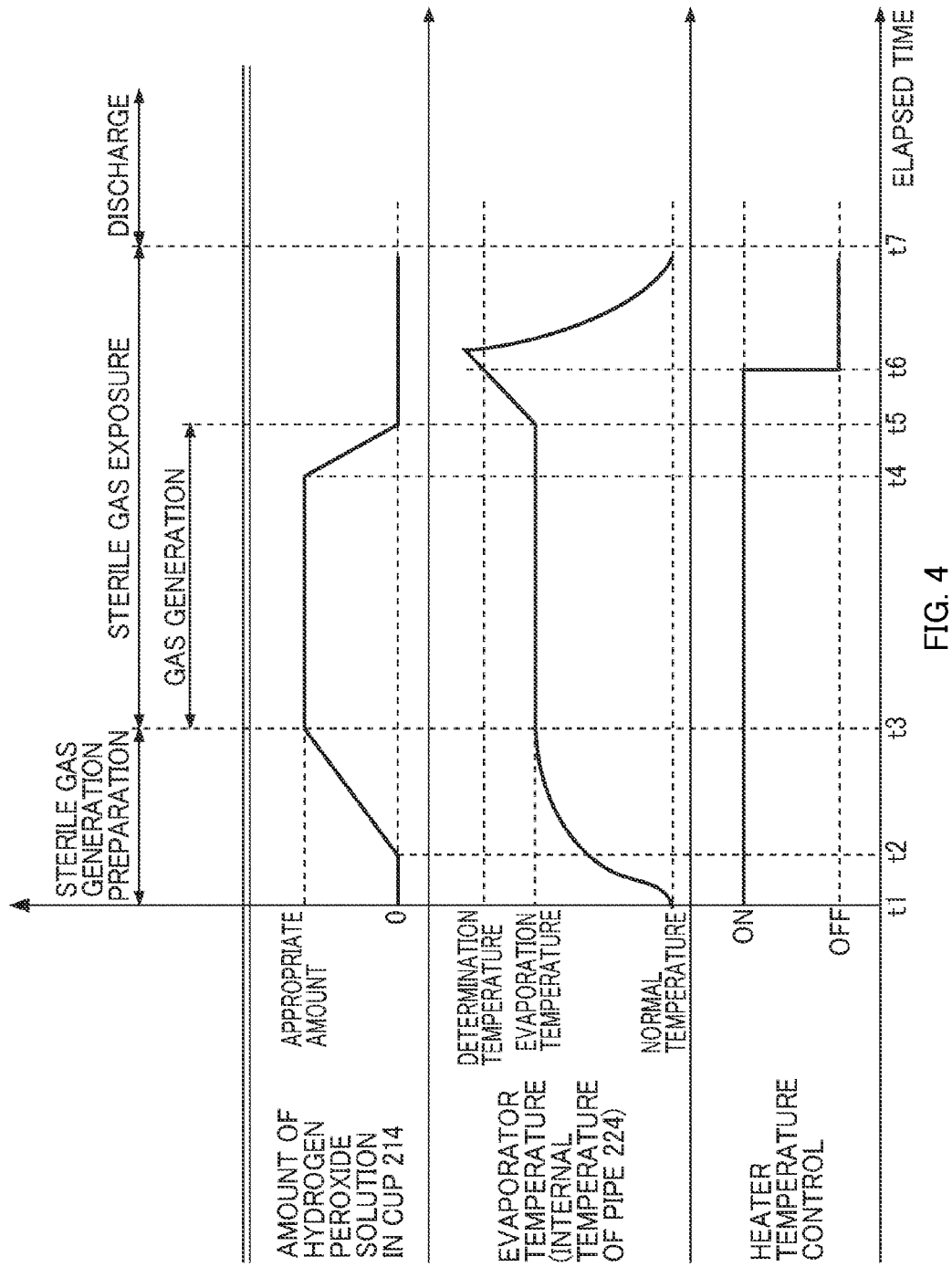
FIG. 4 is a timing chart explaining operations performed in generating sterile gas.

The pretreatment process is a preparation process for generating sterile gas in the sterile gas generator 202 (processes t1 to t3 in FIG. 4).

In the exposure process (processes t3 to t7 in FIG. 4), the working chamber 10 is sterilized by circulating hydrogen peroxide gas fed from the sterile gas generator 202 toward the working chamber 10 and back to the sterile gas generator 202 again. At that time, the three-way valve 44 is switched open for the flow to flow only from path 80 toward path 72 and closed between path 70 and path 72. On the other hand, the three-way valve 52 is switched open for the flow to flow only from path 76 toward path 78 and closed between path 76 and path 82. In this way, a gas flow is formed in the isolator 100 to flow from the three-way valve 44 through the inside of the working chamber 10 and the three-way valve 52 and back to the three-way valve 44, and by means of an operational control of the fan 46, the hydrogen peroxide gas introduced into the working chamber 10 can be circulated in the isolator 100. By controlling this flow path and the fan, the HEPA filters 20 and 22 and paths 74 and 76 can be sterilized as necessary.

In the substitution process (the process at t7 and after in FIG. 4), the gas in the working chamber 10 is substituted by supplying air taken in through the air inlet 42 to the working chamber 10 and pushing out the gas in the working chamber 10. More specifically, in the substitution process, the control unit 90 switches the three-way valve 44 to open only between the air inlet 42 and the working chamber 10 and switches the three-way valve 52 to open only between the working chamber 10 and the discharge port 58. The control unit 90 also turns the fan 46 on. In this way, a gas flow path is formed in the isolator 100, in which air taken in from the air inlet 42 flows from path 70 through the HEPA filter 20 into the working chamber 10 and out from the working chamber 10 through the HEPA filter 22 and discharged from the discharge port 58. As a result, the gas in the working chamber 10 is substituted by air, and the hydrogen peroxide gas in the working chamber 10 is removed from the working chamber 10.

At that time, the hydrogen peroxide gas pushed out of the working chamber 10 is subjected to reduction processing by the sterile substance reduction processing unit 54, so to reduce the outflow of hydrogen peroxide gas from the discharge port 58 to the outside of the isolator 100. Also, in the substitution process, the hydrogen peroxide gas in an area other than the working chamber 10 of the isolator 100 such as those remaining in the gas supply unit 40 or those adsorbed by the HEPA filters 20 and 22 in the flow path used for the previous work are also removed.

According to the isolator 100 described above, the following effects can be obtained.

Since hydrogen peroxide solution atomized by the atomization unit 210 is gasified by the evaporation unit 220, gasification of hydrogen peroxide solution in the evaporation unit 220 progresses quickly, and heat quantity imparted by the heater 222 of the evaporation unit 220 can be reduced. As a result, time required for gasification of the hydrogen peroxide solution can be reduced, and thus, time taken to perform the entire sterilization processing can be reduced. As a result, the work efficiency of the isolator 100 can be improved.

Also, after a predetermined amount of hydrogen peroxide solution is supplied by the pump 264 to the cup 214, detection can be made that the amount of the hydrogen peroxide solution remaining in the cup 214 is nil by determining whether or not the internal temperature of the pipe 224 has reached the predetermined determination temperature. As a result, the temperature of the heater 222 can be controlled without waste, and energy consumption of the isolator 100 can be suppressed. Since the amount of the hydrogen peroxide solution remaining in the cup 214 is nil, it can be confirmed that the predetermined amount of hydrogen peroxide solution required for sterile processing has been atomized, the exposure process can be certainly performed, and reliability of the sterilization effect is improved.

Second Embodiment

Figure 5:
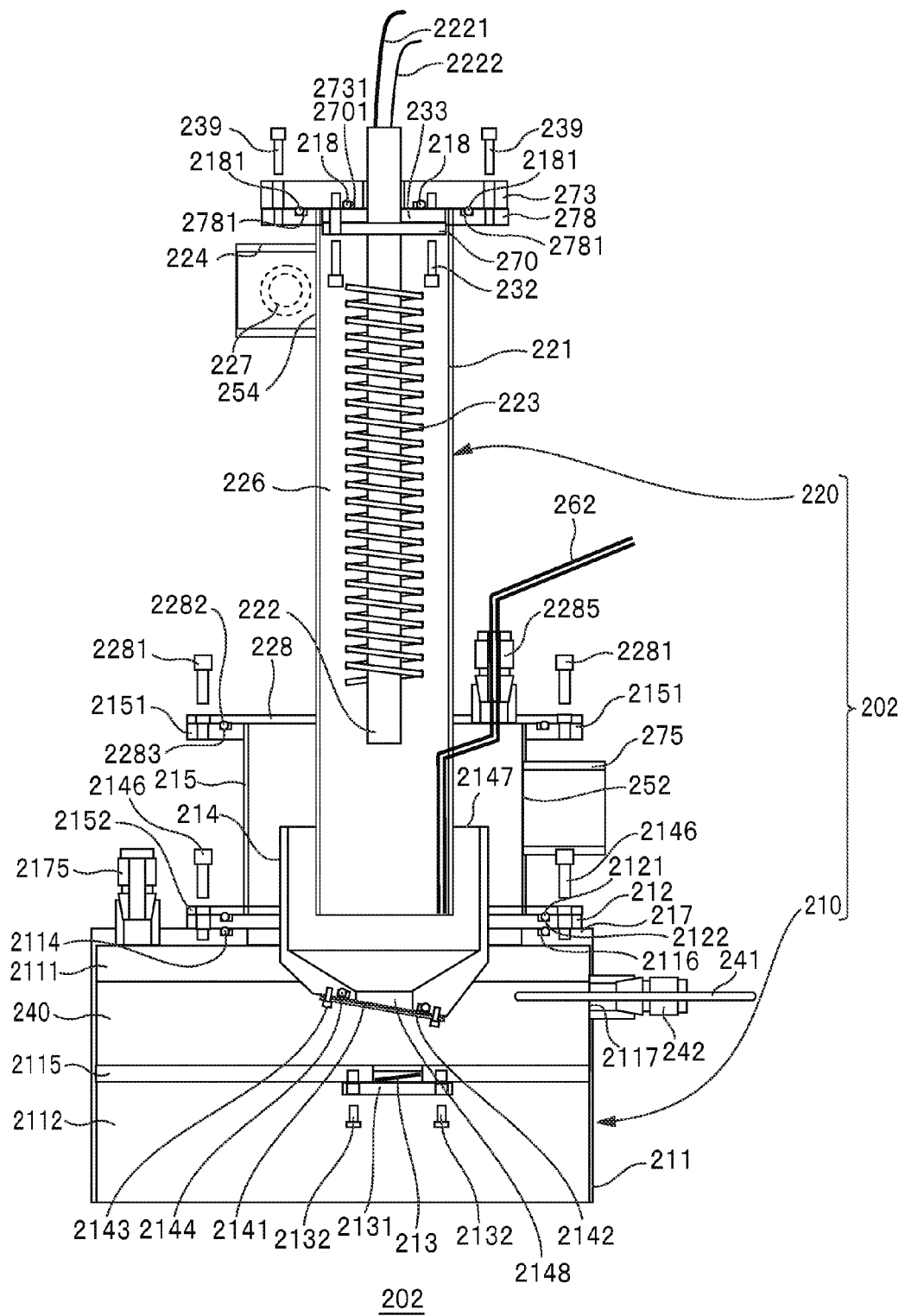
FIG. 5 is a diagram illustrating a configuration of a sterile gas generator of the second embodiment.

The configuration of the isolator 100 described as the second embodiment is similar to that of the isolator 100 in the first embodiment but differs from the first embodiment on a point that the normal of the vibrating plate 2141 of the sterile gas generator 202 is inclined with regard to the vertical direction. FIG. 5 shows the configuration of the sterile gas generator 202, which will be described as the second embodiment. FIG. 5 is a sectional view of the sterile gas generator 202 seen from the side.

Figure 6A:
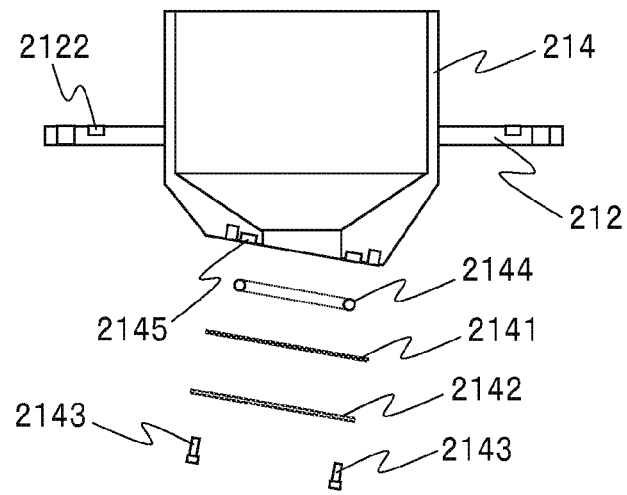
FIG. 6A is an exploded view of the sterile gas generator of the second embodiment including a cup, an O-ring, a vibrating plate, and a flat plate.
Figure 6B:
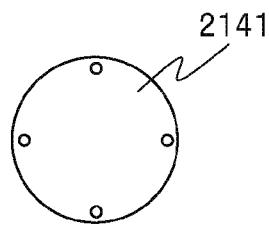
FIG. 6B is a plan view of the vibrating plate of the sterile gas generator of the second embodiment.
Figure 6C:
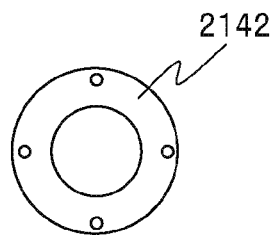
FIG. 6C is a plan view of the flat plate of the sterile gas generator of the second embodiment.

In the sterile gas generator 202 of the second embodiment, as shown in FIG. 5, the normal direction at the center of the vibrating surface of the vibrating plate 2141 is inclined with regard to the vertical direction. By inclining the vibrating plate 2141 from the vertical direction in this way, formation of bubbles (water bubbles when the ultrasound propagation substance 240 is water) causing propagation loss of ultrasound waves on the lower face side of the vibrating plate 2141 can be effectively suppressed. FIG. 6A shows a state in which the cup 214, the O-ring 2144, the vibrating plate 2141, and the flat plate 2142 are disassembled. Also, FIG. 6B shows a plan view of the vibrating plate 2141, and FIG. 6C shows a plan view of the flat plate 2142, respectively.

Note that the vibrating plate 2141 is preferably set so that the normal direction at the center of the vibrating surface does not align with the normal direction of the center of the vibrator surface. By displacing the normal direction of the vibrating surface center of the vibrating plate 2141 from the normal direction of the center of the vibrator surface, the ultrasound waves sent out from the ultrasound vibrator 213 is prevented from directly interfering with a reflection wave reflected from the vibrating plate 2141, and ultrasound waves sent out from the ultrasound vibrator 213 can be efficiently transmitted to the hydrogen peroxide solution.

Third Embodiment

Figure 7:
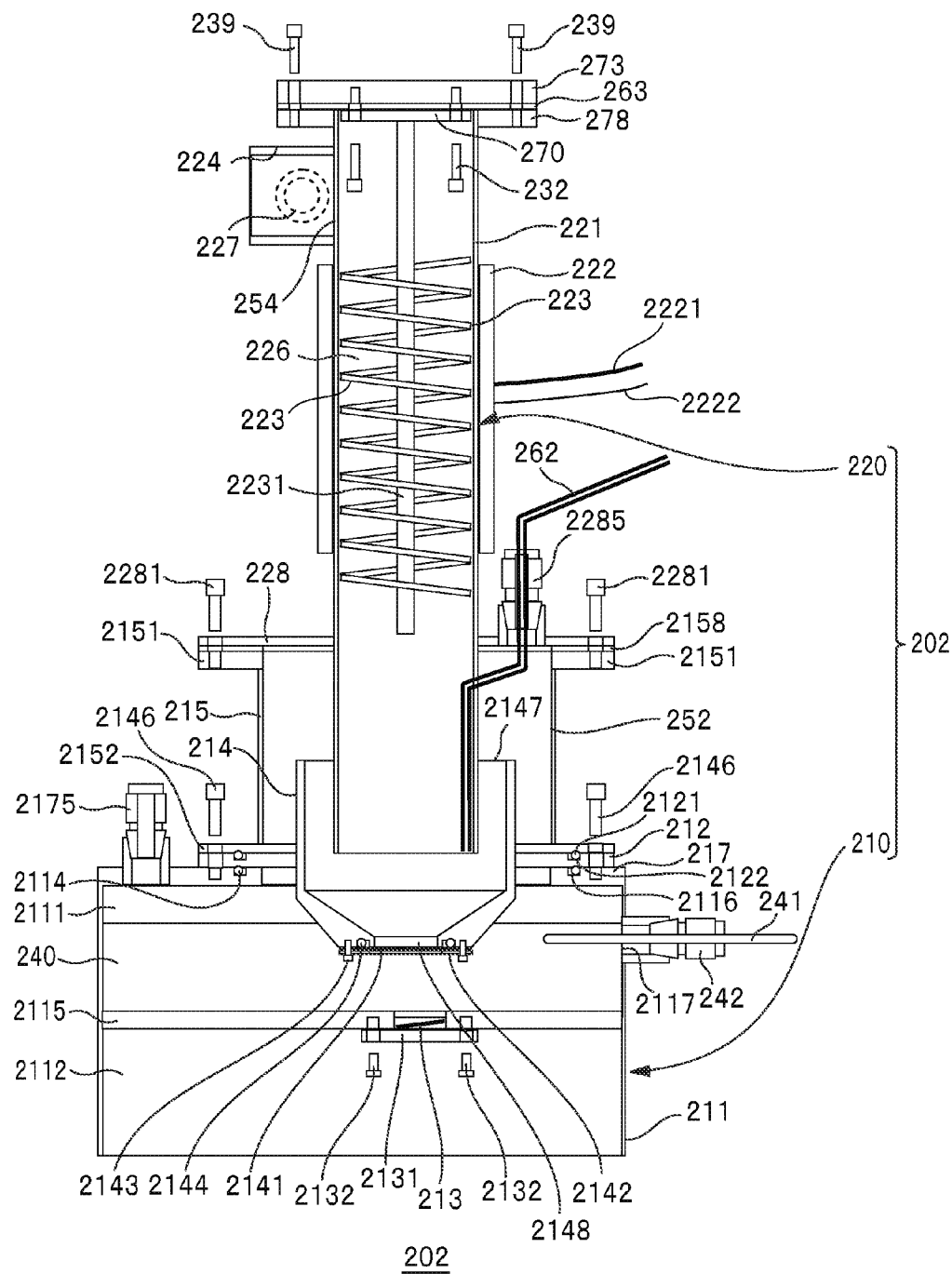
FIG. 7 is a diagram illustrating a configuration of a sterile gas generator of the third embodiment.

The configuration of the isolator 100 described as the third embodiment is similar to that of the isolator 100 of the first embodiment but the configurations of the heater 222 and the fin 223 of the sterile gas generator 202 are different from those of the first embodiment. FIG. 7 shows the configuration of the sterile gas generator 202, which will be described as the third embodiment. FIG. 7 is a sectional view of the sterile gas generator 202 seen from the side.

The heater 222 being a heater element was disposed inside the heat pipe 221 in the first embodiment however, in the third embodiment, the heater 222 is not disposed inside the heat pipe 221 but only a configuration corresponding to the fin 223 is arranged therein, and the heater 222 is disposed around the side face of the heat pipe 221 outside the heat pipe 221. The fin 223 is disposed along a shaft member 2231 to extend in the vertical direction of the heat pipe 221. At an upper end of the shaft member 2231, the flange 270 is disposed. In the present embodiment, a band heater is used as the heater 222, which is wound around the side face of the heat pipe 221.

In the third embodiment shown in FIG. 7, fin 223 spirally extending in the vertical direction of the heat pipe 221 is provided. The outer diameter of the fin 223 is approximately the same as the inner diameter of the heat pipe 221. The fin 223 is heated by radiation heat of the heater 222 disposed around the side face of the heat pipe 221, and the entire fin 223 is heated by heat transfer in the fin 223. Hydrogen peroxide solution rising from the bottom to the top of the heat pipe 221 is heated by the fin 223 and guided by the fin 223 to the proximity of the outer wall of the heat pipe 221 and further heated by radiation heat of the heater 222. In this way, hydrogen peroxide solution can be heated efficiently and evaporated quickly according to the sterile gas generator 202 of the third embodiment.

Fourth Embodiment

Figure 8:
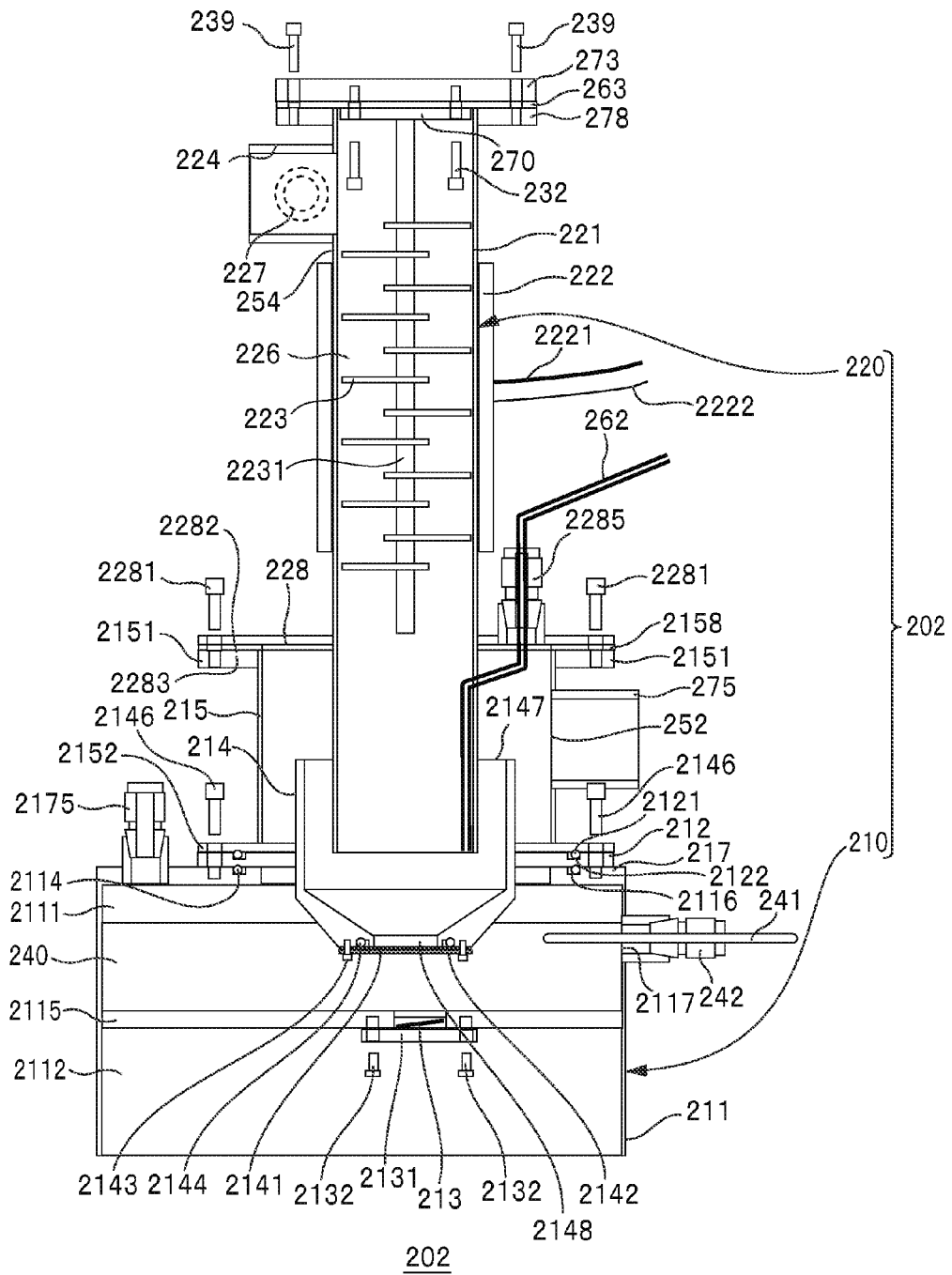
FIG. 8 is a diagram illustrating a configuration of a sterile gas generator of the fourth embodiment.

The configuration of the isolator 100 described as the fourth embodiment is similar to that of the isolator 100 of the third embodiment but the configuration of the fin 223 of the sterile gas generator 202 is different from that of the third embodiment. FIG. 8 shows the configuration of the sterile gas generator 202 described as the fourth embodiment. FIG. 8 is a sectional view of the sterile gas generator 202 seen from the side.

In the third embodiment, the helical fin 223 was provided to extend in the vertical direction of the heat pipe 221, but in the fourth embodiment, the fin 223 is configured by a substantially semicircular plate member made of material such as stainless steel. Each of the fins 223 are arranged with predetermined intervals therebetween in the vertical direction of the heat pipe 221 and with alternative adjacent fins 223 opposing each other with each of the faces directed in the horizontal direction. The diameter of each fin 223 is approximately the same as the inner diameter of the heat pipe 221.

Figure 9:
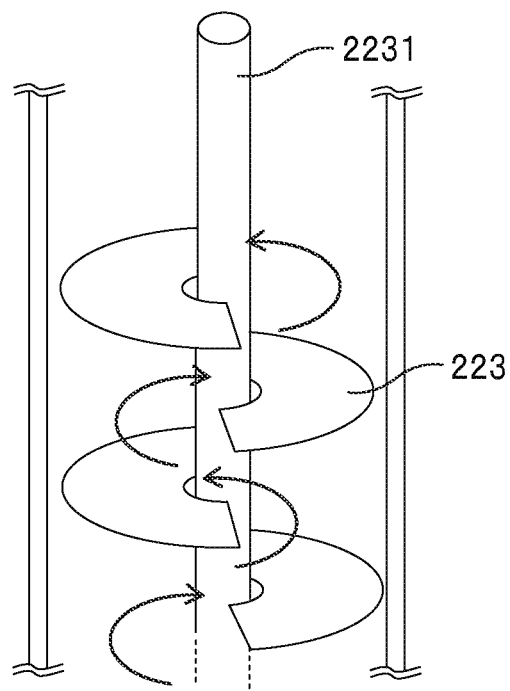
FIG. 9 is a diagram for explaining a flow of hydrogen peroxide flowing inside a heat pipe in the sterile gas generator of the fourth embodiment.

As shown in FIG. 9, hydrogen peroxide solution flowing inside the heat pipe 221 flows from the lower part to the upper part of the heat pipe 221 through space partitioned by the adjacent fins 223 (arrows in the figure indicate the flow of the hydrogen peroxide solution). Each fin 223 is heated by radiation heat of the heater 222 disposed around the side face of the heat pipe 221, and the entirety of the fins 223 are heated by heat transfer in each fin 223 and the shaft member 2231. The hydrogen peroxide solution rising from the lower part to the upper part of the heat pipe 221 is heated by the fin 223 and guided to the proximity of the outer wall of the heat pipe 221 by the fin 223 to be heated by the radiation heat of the heater 222. In this way, the hydrogen peroxide solution can be heated efficiently and evaporated quickly according to the sterile gas generator 202 of the fourth embodiment.

Fifth Embodiment

Figure 10A:
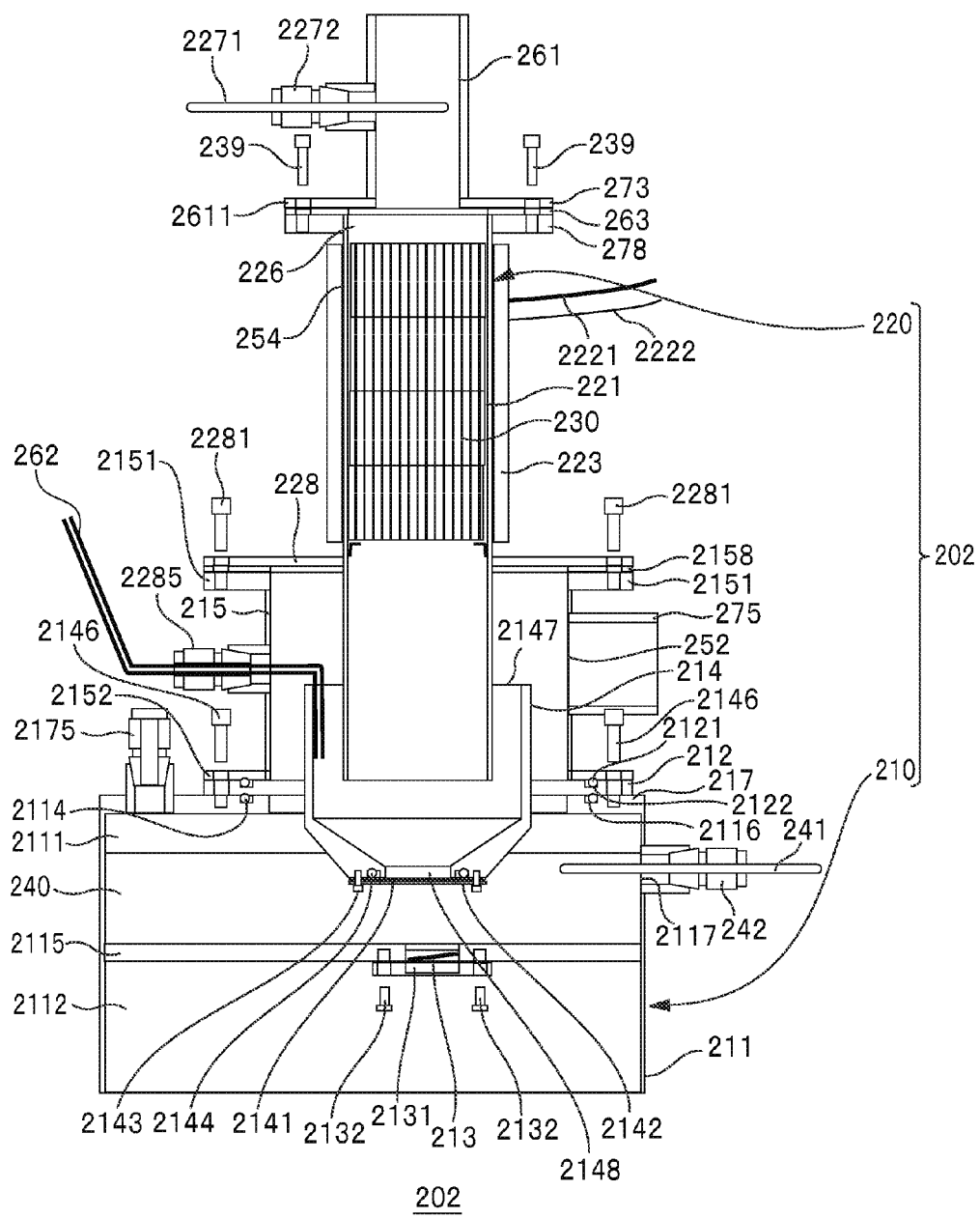
FIG. 10A is a diagram illustrating a configuration of a sterile gas generator of the fifth embodiment.
Figure 10B:
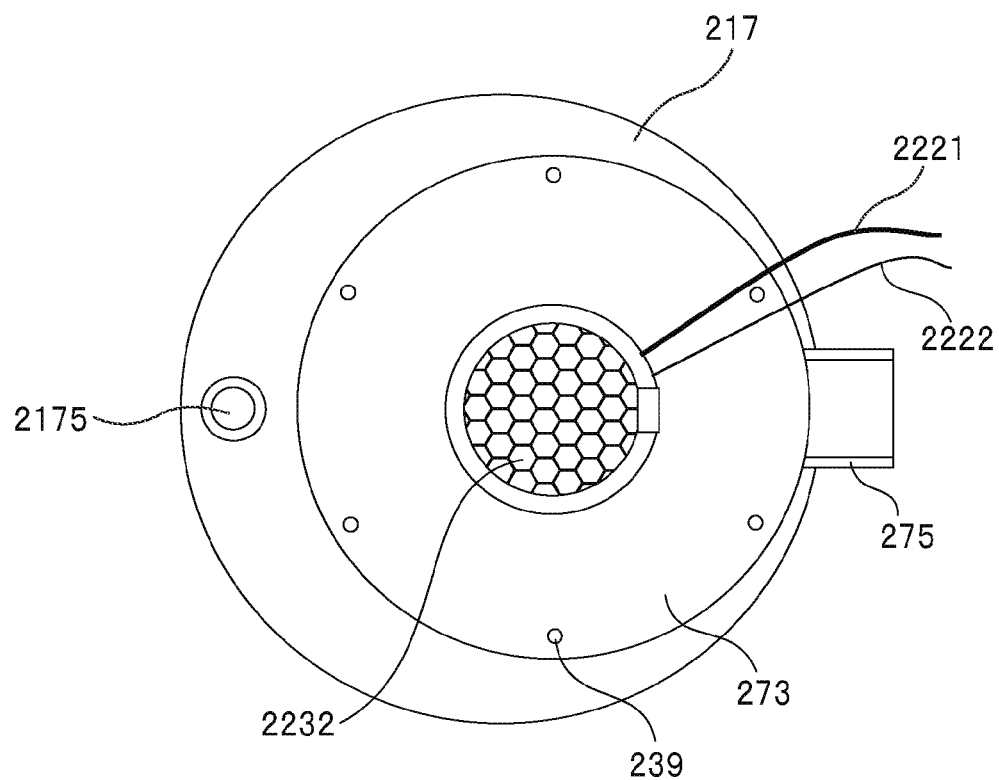
FIG. 10B is a diagram (partially cut away) of the sterile gas generator of the fifth embodiment seen from above.

The configuration of the isolator 100 described as the fifth embodiment is similar to that of the isolator 100 of the first embodiment but the configuration of the fin 223 of the sterile gas generator 202 is different from that of the first embodiment. FIGS. 10A and 10B show the configuration of the sterile gas generator 202 described as the fifth embodiment. FIG. 10A is a sectional view of the sterile gas generator 202 seen from the side, and FIG. 10B is a diagram (partially cutaway) of the sterile gas generator 202 seen from above.

The heater 222 being a heating element was disposed inside the heat pipe 221 in the first embodiment however, in the fifth embodiment, a honeycomb structural body 230 (rectification plate), extending in the vertical direction inside the heat pipe 221, through which a plurality of flow paths 2232 with hexagonal sections formed for flowing hydrogen peroxide solution therein are arranged inside the heat pipe 221 with the heater 222 disposed around the side face of the heat pipe 221 outside the heat pipe 221. The outer diameter of the structural body 230 is approximately the same as the inner diameter of the heat pipe 221. In the present embodiment, a band heater is used as the heater 222, which is wound around the side face of the heat pipe 221.

Hydrogen peroxide solution flowing inside the heat pipe 221 flows from the lower part to the upper part of the heat pipe 221 through the flow paths 2232 of the structural body 230. The structural body 230 is heated by radiation heat of the heater 222 disposed around the side face of the heat pipe 221, and the entire structural body 230 is heated by heat transfer inside the structural body 230. The hydrogen peroxide solution rising from the lower part to the upper part in the heat pipe 221 through each flow path 2232 of the structural body 230 is heated by heat supplied from the wall of each flow path 2232. In this way, hydrogen peroxide solution can be heated efficiently and evaporated quickly according to the sterile gas generator 202 of the fifth embodiment.

As shown in FIG. 10A, at an upper part of the heat pipe 221 of the sterile gas generator 202 of the fifth embodiment, a cylindrical discharge pipe 261 communicating with the heat pipe 221 is disposed coaxially with the heat pipe 221. A flange 2611 is disposed at a lower part of the discharge pipe 261 and this flange 2611 is fixed to the flange 278 on the upper surface of the heat pipe 221 with screws 239. In this way, resistance of the flow path is reduced as compared with the structure in the first embodiment or the like by providing the heat pipe 221 and the discharge pipe 261 coaxially. Thus hydrogen peroxide solution can be flown efficiently even if the honeycomb structural body 230 is provided inside the heat pipe 221.

Note that, in order to prevent heat of the heat pipe 221 from escaping to the discharge pipe 261 side, an insulation packing 263 is interposed between the flange 2611 of the discharge pipe 261 and the flange 278 at the upper part of the heat pipe 221. And in order to prevent heat of the heat pipe 221 from escaping to the cylindrical member 215 side, an insulation packing 2158 is interposed between the flange 228 at the lower part of the heat pipe 221 and the flange 2151 of the cylindrical member 215. Also, in the sterile gas generator 202 of the fifth embodiment, the temperature measuring unit 227 including the thermometer 2271 and the fitting 2272 holding the same is disposed on the side face of the discharge pipe 261. Further, the drain 262 is disposed on the side face of the cylindrical member 215 through the fitting 2285.

Sixth Embodiment

The configuration of the isolator 100 described as the sixth embodiment, is similar to the configuration of the isolator 100 of the first embodiment but differs from first embodiment on a point that a plurality of substantially semicircular (a shape similar to that of the fin 223 in the fourth embodiment, for example) fins 229 made of a material such as stainless steel are provided with intervals therebetween in the vertical direction of the heat pipe 221 of the sterile gas generator 202.

Figure 11:
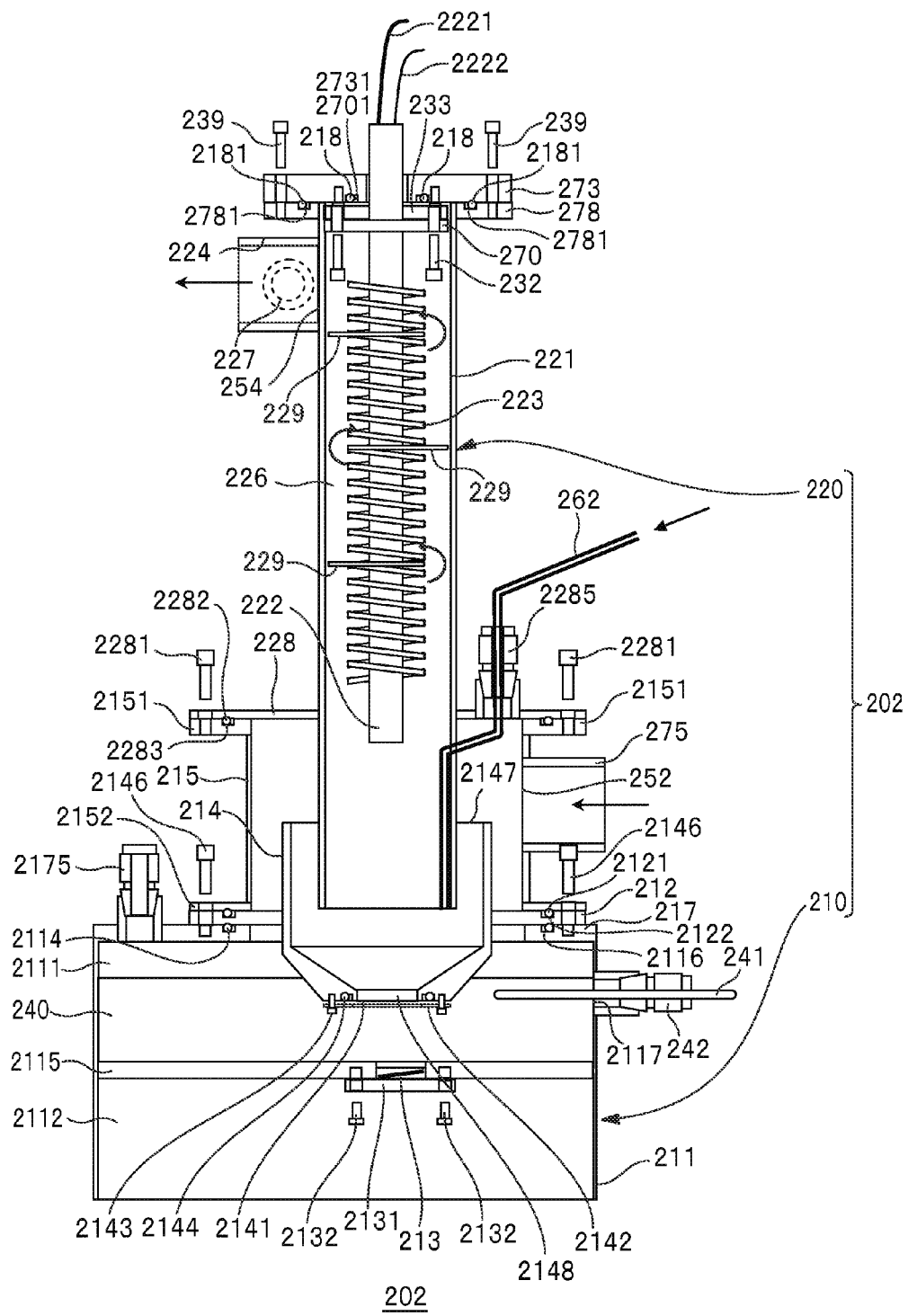
FIG. 11 is a diagram illustrating a configuration of a sterile gas generator of the sixth embodiment.

FIG. 11 shows the configuration of the sterile gas generator 202 described as the sixth embodiment. FIG. 11 is a sectional view of the sterile gas generator 202 seen from the side. As shown in FIG. 11, each of the fins 229 are arranged with predetermined intervals therebetween in the vertical direction of the heat pipe 221 with alternative adjacent fins 229 opposing each other with each of the faces directed in the horizontal direction. The outer diameter of each fin 229 is approximately the same as the inner diameter of the heat pipe 221, and the outer peripheral edge of each fin 229 substantially reaches an inner periphery of the heat pipe 221. Also, the inner peripheral edge of each fin 229 comes in to contact with the outer periphery of the heater 222.

In FIG. 11, arrows in the heat pipe 221 indicate the flow of hydrogen peroxide solution. The hydrogen peroxide solution flowing inside the heat pipe 221 flows from the lower part to the upper part of the heat pipe 221 through a space partitioned by the adjacent fins 229. The flow of hydrogen peroxide solution flowing inside the heat pipe 221 is bent to the horizontal direction by the fins 229, by which the hydrogen peroxide solution from a direction perpendicular to the axis of the heater 222 is flown to the periphery of the heater 222.

The heater 222 and the fin 223 shown in FIG. 11 have a structure such that the heat transfer efficiency is improved by applying substance to be heated from a direction perpendicular to the axis of the heater 222. In the above-described manner, the efficiency of heat transfer from the heater 222 and the fin 223 to the hydrogen peroxide solution is improved by making the hydrogen peroxide solution flow in the periphery of the heater 222 from a direction perpendicular to the axis of the heater 222. Note that, hydrogen peroxide solution is also heated by the fin 229, which also improves the evaporation efficiency of the hydrogen peroxide solution.

Seventh Embodiment

Figure 12A:
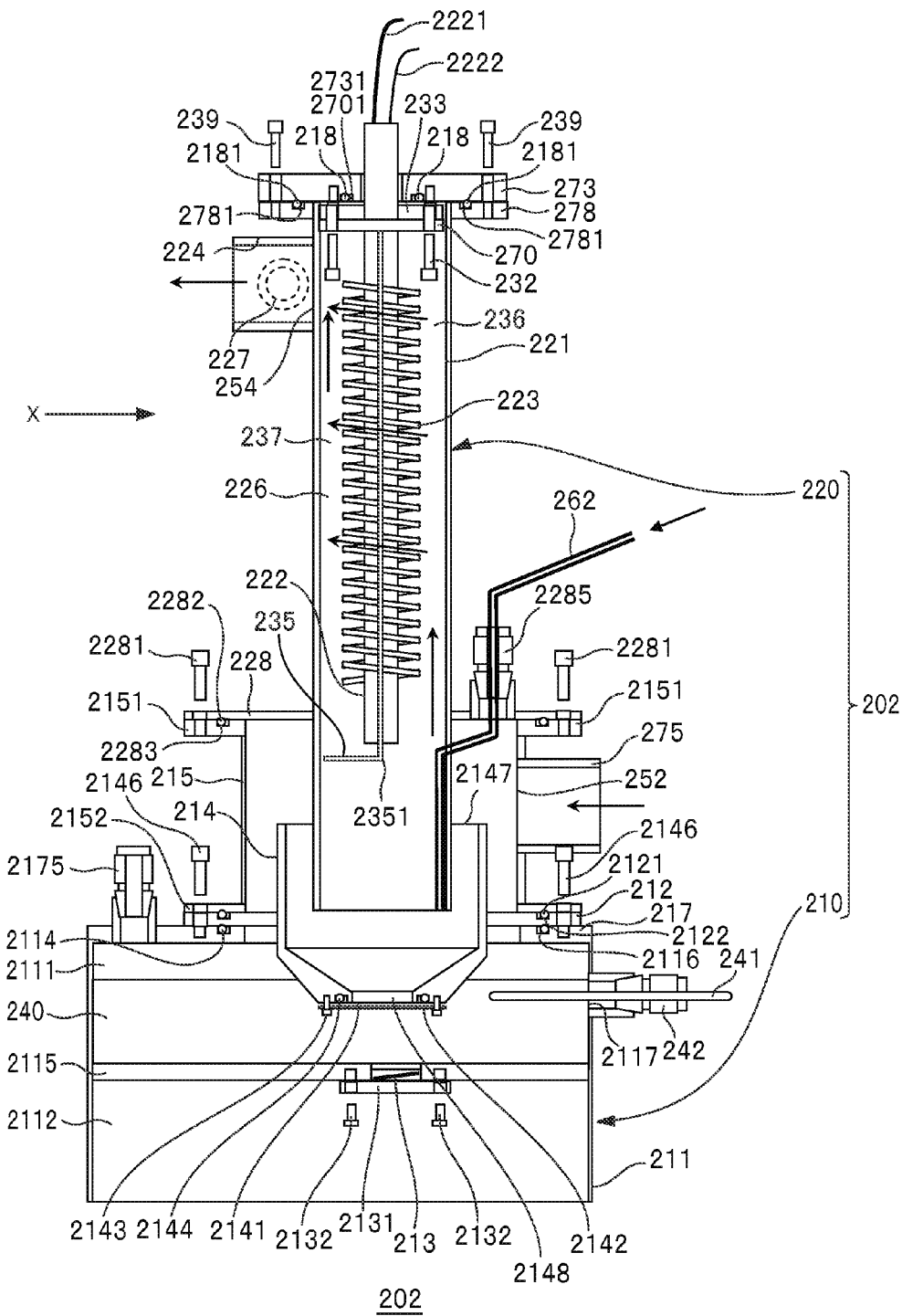
FIG. 12A a diagram illustrating a configuration of a sterile gas generator of the seventh embodiment.
Figure 12B:
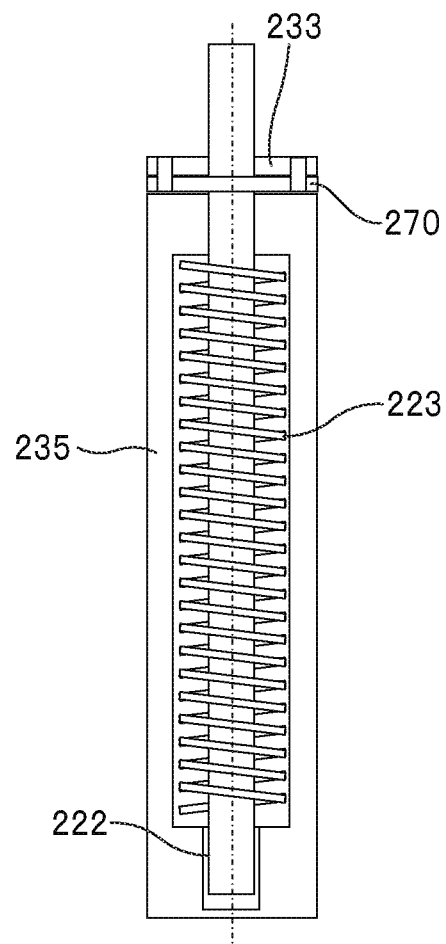
FIG. 12B is a diagram illustrating a component of the sterile gas generator of the seventh embodiment.

The configuration of the isolator 100 described as the seventh embodiment is similar to that of the isolator 100 of the first embodiment but differs from the first embodiment on a point that a baffle plate 235 made of material such as stainless steel is provided so as to surround the periphery of the heater 222 of the sterile gas generator 202 inside the heat pipe 221. FIGS. 12A and 12B show the configuration of the sterile gas generator 202 described as the seventh embodiment. FIG. 12A is a sectional view of the sterile gas generator 202 seen from the side, and FIG. 12B is a partial view of the configuration around the heater 222 of the sterile gas generator 202 seen from a direction indicated by arrow X in FIG. 12A.

The baffle plate 235 is disposed to surround the periphery of the heater 222, and the vertical center line of the baffle plate 235 aligns with the axis of the heat pipe. The outer diameter of the baffle plate 235 in the horizontal direction (direction perpendicular to the axis of the heat pipe 221) is substantially equal to the inner diameter of the heat pipe 221, and the peripheral edge of the baffle plate 235 substantially reaches the inner wall of the heat pipe 221 except for a part on the lower side thereof.

As shown in FIG. 12A, the lower side portion of the baffle plate 235 is bent at a predetermined height from the lower end thereof, and the distal end portion of the baffle plate 235 that is bent substantially reaches the inner wall of the heat pipe 221. The outer peripheral edge of the bent portion of the baffle plate 235 (hereinafter referred to as the bent portion 2351) has a semicircular shape.

As shown in FIG. 12B, a portion of the baffle plate 235 where the heater 222 and the fin 223 are located is opened. As shown in FIG. 12A, the internal space of the heat pipe 221 is divided into two by the baffle plate 235, that is, into a space of the heat pipe 221 on the side where the bent portion 2351 is not present (a semi-columnar space, hereinafter referred to as a first space 236) and a space formed above the bent portion 2351 (hereinafter referred to as a second space 237).

Hydrogen peroxide solution rising from the lower part to the upper part of the heat pipe 221 firstly flows from a space formed below the lower end of the baffle plate 235 in the heat pipe 221 into the first space 236 and then flows into the second space 237 through a gap between the heater 222 and the fin 223. In the sterile gas generator 202 of the seventh embodiment, hydrogen peroxide solution is made to pass through a gap between the heater 222 and the fin 223 without fail to heat the hydrogen peroxide solution uniformly. Therefore, hydrogen peroxide solution can be heated efficiently and evaporated quickly.

Note that a part of the baffle plate 235 can be made to contact the heater 222 or the fin 223 so that the baffle plate 235 is heated by the heater 222. In this way, hydrogen peroxide solution is also heated by flowing through the peripheral area of the baffle plate 235 so that evaporation of hydrogen peroxide solution can be further promoted.

The above embodiments of the present invention are simply for facilitating the understanding of the present invention and are not in any way to be construed as limiting the present invention. The present invention may variously be changed or altered without departing from its spirit and encompass equivalents thereof.

What is claimed is:

1. A sterile substance supplying apparatus comprising:
an atomization unit including a tubular reservoir unit having an opening at a top portion thereof, the tubular reservoir unit configured to reserve hydrogen peroxide in a bottom portion thereof, and an ultrasound vibrator configured to impart ultrasound vibration to the hydrogen peroxide reserved in the reservoir unit to be atomized;
an evaporation unit provided above the reservoir unit, including a hollow cylindrical heat pipe configured to allow the hydrogen peroxide atomized by the atomization unit to flow therethrough from a lower part to an upper part, the evaporation unit configured to heat the hydrogen peroxide atomized by the atomization unit to be evaporated, the hollow cylindrical heat pipe having a diameter smaller than that of the opening of the tubular reservoir unit, the hollow cylindrical heat pipe disposed such that a lower end portion thereof is set at a position between the opening at the top portion of the tubular reservoir unit and the bottom portion of the tubular reservoir unit;
a cylindrical connecting member connecting the tubular reservoir unit and the hollow cylindrical heat pipe so as to cover the opening of the tubular reservoir unit around the hollow cylindrical heat pipe;
a hydrogen peroxide supply port configured to allow the hydrogen peroxide to be supplied to the tubular reservoir unit;
a carrier gas supply port provided at the cylindrical connecting member in order to flow in carrier gas so that the carrier gas flows into the opening of the tubular reservoir unit, around the hollow cylindrical heat pipe, and into an interior of the hollow cylindrical heat pipe as well as being mixed with the hydrogen peroxide atomized by the atomization unit; and
a container portion configured to reserve a substance for transmitting the ultrasound vibration generated by the ultrasound vibrator,
the bottom portion of the tubular reservoir unit provided with a metal vibrating plate configured to transmit to the hydrogen peroxide the ultrasound vibration transmitted through the substance,
the position of the lower end portion of the hollow cylindrical heat pipe set at a height at which the hydrogen peroxide is blocked, by a side face of the hollow cylindrical heat pipe, from scattering from the bottom portion of the tubular reservoir unit toward the opening at the top portion of the tubular reservoir unit by the ultrasound vibration.

2. The sterile substance supplying apparatus according to claim 1, further comprising
an annular flat plate provided on a lower face of the metal vibrating plate; wherein
the metal vibrating plate includes a peripheral edge fixed to a bottom face of the tubular reservoir unit along with the annular flat plate, and is detachably mounted to the tubular reservoir unit.

3. The sterile substance supplying apparatus according to claim 1, wherein
the evaporation unit includes: a heater configured to heat the hydrogen peroxide; and a heat transfer body provided inside the hollow cylindrical heat pipe, the heat transfer body configured to transmit heat of the heater to the hydrogen peroxide, and wherein
the heater is provided around a side face of the hollow cylindrical heat pipe, and wherein
the heat transfer body includes a plate-shaped helical fin extending in a vertical direction of the hollow cylindrical heat pipe, and wherein
an outer diameter of the plate-shaped helical fin is substantially equal to an inner diameter of the hollow cylindrical heat pipe.

4. The sterile substance supplying apparatus according to claim 1, wherein
the evaporation unit includes: a heater configured to heat the hydrogen peroxide; and a heat transfer body provided inside the hollow cylindrical heat pipe, the heat transfer body configured to transmit heat of the heater to the hydrogen peroxide, and wherein
the heater is provided around a side face of the hollow cylindrical heat pipe, and wherein
the heat transfer body includes a plurality of substantially semicircular fins, and wherein
each of the plurality of substantially semicircular fins is arranged with a predetermined interval in a vertical direction of the hollow cylindrical heat pipe so that the plurality of substantially semicircular fins face with respect to each other alternately, and wherein
an outer diameter of each of the plurality of substantially semicircular fins is substantially equal to an inner diameter of the hollow cylindrical heat pipe.

5. The sterile substance supplying apparatus according to claim 1, wherein
the evaporation unit includes: a heater configured to heat the hydrogen peroxide; and a heat transfer body provided inside the hollow cylindrical heat pipe, the heat transfer body configured to transmit heat of the heater to the hydrogen peroxide, and wherein
the heater is provided around a side face of the hollow cylindrical heat pipe, and wherein
the heat transfer body includes a honeycomb structural body extending in a vertical direction of the heat pipe in which a plurality of flow paths with hexagonal sections are formed inside to allow the hydrogen peroxide to flow therethrough, and wherein
an outer diameter of the honeycomb structural body is substantially equal to an inner diameter of the hollow cylindrical heat pipe.

* * * * *